United States Patent [19]
Fanget et al.

[11] Patent Number: 5,731,187
[45] Date of Patent: Mar. 24, 1998

[54] PROCESS FOR PREPARING HEPATITIS A (HAV) ANTIGENS AND VACCINES

[75] Inventors: Bernard Fanget, Fleurieux Sur L'Arbresle; Alain Francon, Bessenay, both of France

[73] Assignee: Pasteur Merieux Serums Et Vaccins Societe Anonyme, France

[21] Appl. No.: 136,580

[22] Filed: Oct. 13, 1993

[30] Foreign Application Priority Data

Oct. 14, 1992 [FR] France ................................ 92-12285

[51] Int. Cl.$^6$ .............................. C12N 7/00; C12N 7/02; A61K 39/29
[52] U.S. Cl. ..................... 435/235.1; 435/239; 435/89; 435/948; 424/226.1; 424/189.1
[58] Field of Search ............................ 435/235.1, 239, 435/948; 424/89, 226.1

[56] References Cited

FOREIGN PATENT DOCUMENTS 0468702   1/1992   European Pat. Off. .

OTHER PUBLICATIONS

Mussgay et al. J. Gen. Virol. (1973), 19, 89–101.
Coulepis et al. Intervirology 18: 107–127, 1982.
Welling–Wester et al J. Chromatography 646:37–44, 1993.
Welling et al, J. Chromatography 359:307–314, 1986.
Welling –Wester et al J. Chromatography 476:477–485, 1989.
Calam et al, J Chromatography 296:285–292, 1984.
Black et al, J. Gen. Virol. 32, 509–518, 1976.
Armon et al, Can. J. Microbiol. 34:651–655, 1988.
D'Hundt, E. Vaccine 10, Suppl 1 548–553, 1992.
Alligen H. American Laboratory, Oct. 1975 (7 pages).
England et al, Methods in Enzymology 182:285–300, 1990.

*Primary Examiner*—Paula K. Hutzell
*Assistant Examiner*—Kualid Masood
*Attorney, Agent, or Firm*—Bierman, Muserlian and Lucas

[57] ABSTRACT

Process for preparing hepatitis A (HAV) antigens and vaccines.

The HAV virus is multiplied on competent cells, the infected cells are lysed, the supernatant is recovered and the purification is carried out by a chromatographic procedure on an anion-exchange support and a gel filtration procedure, the purification procedures being carried out in the presence of a detergent, and the chromatographic procedure being carried out under conditions which retain the virions or viral capsids, which are then eluted.

9 Claims, No Drawings

PROCESS FOR PREPARING HEPATITIS A (HAV) ANTIGENS AND VACCINES

The present invention relates to a new process for preparing hepatitis A virus (HAV) antigens and vaccines.

The preparation of vaccines which are effective against hepatitis A is now known. On the other hand, advances remain to be made in the industrial field of culture of the HAV virus and purification of the capsid antigens of this picornavirus.

The initial processes for the partial purification of HAV virions having proved too expensive or unsatisfactory for the production of vaccines, application EP-A-0,302,692 recommended subjecting the cells having served for the multiplication of the HAV virus, lysed beforehand, to organic solvent extraction procedures combined with polyethylene glycol (PEG) precipitations. The extract may then be optionally subjected to a chromatography on an anion-exchange support allowing the viral capsids to pass through, followed by a gel filtration. This process is presented as having the advantage of avoiding any use of detergents.

Subsequently, application EP-A-0,468,702 combined with this same process a second chromatographic step on an anion-exchange support under conditions which make it possible to retain the viral capsids which are then eluted, the eluate being subjected to the gel filtration step.

These processes have the disadvantage of being complicated and requiring the use of organic solvents.

The present invention proposes to overcome the disadvantages of the prior art and to provide a new process for preparing hepatitis A antigens and vaccines.

The subject of the invention is a process for preparing hepatitis A antigens and vaccines in which the HAV virus is multiplied on competent cells, the infected cells are lysed preferably by sonication, the supernatant is recovered and the purification is carried out by a chromatographic procedure on an anion-exchange support and a gel filtration procedure, characterized in that the purification procedures are carried out in the presence of a detergent, preferably Tween 80, and in that the chromatographic procedure is carried out under conditions which retain the virions or viral capsids, which are then eluted.

In the present invention, the presence of the detergent is especially designed to avoid the phenomena of adsorption of the capsids or virions. The Tween 80 (sorbitan mono-9-octadecanoate) is remarkably effective, preferably at concentrations of 0.001 to 5%, especially of 0.1%. Consequently, the invention also relates to the use of detergents, which, for this function, are equivalent to Tween 80.

The use of the detergent according to the invention makes it possible to avoid the extraction steps of the prior art and to carry out, after simply filtering the lysis supernatant, a single ion-exchange chromatographic step on a support which retains the vital capsids whereas the protein and nucleic contaminants are removed in the effluent. The antigenic capsids are then easily recovered by elution.

Preferably, the chromatographic support consists of DEAE-Spherodex (Sepracor IBF DEAE-Spherodex LS Ref. 61002) but supports such as Pharmacia DEAE-Sepharose can also be used. Preferably, the chromatographic column is equilibrated with buffer containing the detergent, especially Tween 80; the eluent may also contain the detergent.

The eluate is preferably concentrated after the chromatography, especially by ultrafiltration.

The eluate, preferably concentrated, is then subjected to the gel filtration, preferably on Sepharose CL 6B, in the presence of the detergent.

The viral peak obtained can then be again concentrated and then inactivated by a customary process.

Other advantages and characteristics of the invention will emerge on reading the following description, made by way of non-restrictive example.

EXAMPLE

1) Culture of the Cells

The cells used are human deploid cells of the MRC5 line. The working stock consists of the 16th passage.

The vial containing the working stock is thawed and transferred into a culture flask F 75 cm$^2$ into which the cell culture medium is introduced in the presence of foetal calf serum (FCS) and the culture dish is placed in an oven at 37° C. When the cells are confluent in the culture dishes, a trypsinization procedure is carried out.

The culture medium is removed from the culture container; the cell layer is rinsed with a PBS solution and the cells are detached by a dilute trypsin solution, after which cell culture medium is again introduced, the cells are dispersed in the medium and the cellular suspension obtained is distributed into the new culture containers. The culture is then carried out from the 18th to the 38th passage using increasingly larger containers, for example by going from a 75 cm$^2$ flask during the 18th passage up to the CF 40 (cell factory consists of 40 units of 600 cm$^2$) multitray container using, for intermediate passages, the customary culture containers corresponding to the increasing volumes to be treated. After 24 h of culture at 37° C. the culture medium of the CF 40 containers of the 38th passage is removed by aspiration and replaced by an inoculum consisting of cell culture medium containing foetal calf serum and quantity of hepatitis A virus so as to have a multiplicity of infection of between 0.01 and 1. Each CF 40 receives 8 liters of this medium.

The CF 40 containers are then replaced in the oven (temperature of 35° C.) and the viral propagation is carried out in 21 days with medium changes after 8 days of culture with medium containing 5% calf serum, then after 16 days with FCS-free medium. The virus is harvested after 21 days of culture.

3) Crude Harvest

On the day of the harvest, the CF 40 containers are carefully examined and possible suspect CF 40 containers are eliminated.

The supernatant culture liquid is removed.

The cellular layer is rinsed twice with two liters of PBS solution.

The cellular layer is then rinsed with 2000 ml of trypsin-EDTA solution.

The CF 40 containers are replaced in the oven at 35° C. for 5 minutes.

1000 ml of 20 mM phosphate buffered solution, pH 7.50, are poured into each CF container, the CF containers are shaken so as to detach all the cells from the culture surface and the cellular suspension is then recovered. The CF containers are then rinsed twice with 1 liter of phosphate buffer.

The cellular suspension recovered (volume of about 40 liters for 12 CF 40 containers) is homogenized and treated continuously with ultrasound at a frequency of 20 KHz in an incubation tank with a flow rate of between 0.5 and 10 ml/second.

After treatment, the cellular suspension is centrifuged at low speed for 30 minutes at 2000 rpm.

The supernatant recovered constitutes the crude harvest.

4) Addition of the Detergent

After removing control samples, a Tween 80 solution is added to the crude harvest tank so as to adjust the final Tween 80 content to 0.1%.

The solution is left stirring overnight at +4° C.

The harvest is then filtered through 0.45 and 0.2μ Durapore-type filters.

This solution therefore constitutes the filtered harvest.

5) Chromatography

The DEAE-Spherodex gel diethylaminoethyl anion exchange chromatographic support or resin) is loaded into a column with 0.1N HCl and prepared by passing 20 mM phosphate buffer, pH 7.5, then a solution of 2 % formalin 2 g/l NaCl and then 1 M NaCl.

In order to equilibrate the column and then carry out the chromatography, 20 mM $PO_4$ buffer, pH 7.5, 0.1% Tween 80is passed until perfect equilibration of pH and osmolality are obtained; the sample, whose osmolality should not exceed 280 mOsm, is passed; 20 mM $PO_4$ buffer, 0.5M NaCl pH 7.5, 0.1% Tween 80 is passed. This procedure allows elution of the virus.

The flow rate is of the order of 45 cm/h.

6) Concentration

The material used is a Pellicon-type ultrafiltration cell equipped with Sartorius ULTRASART II cassettes made from cellulose ester (molecular weight cut-off 10,000 daltons).

The entire installation, cassette, module and piping is sterilized by means of a 5% hydrogen peroxide solution.

The entire installation is rinsed with 20 liters of 20 mM phosphate buffer pH=7.5, 0.1% Tween 80.

The eluate from the DEAE-Spherodex column, fraction in 20 mM phosphate, 0.5M NaCl 0.1% Tween 80, containing the virus is concentrated.

The final volume after rinsing the membranes is adjusted to 1 liter.

7) Gel Filtration

A Pharmacia K215/100 column, filled with 26.5 liters of Sepharose 6B CL gel, is used. Gel height: 73 cm.

The entire installation Column, piping, detector, is sterilized by passing a 2% formalin solution, 2% NaCl, flow rate 1.7 l/h.

The column is washed and equilibrated by means of 20 mM phosphate solution pH=7.5, 0.1% Tween 80 for 48 hours, flow rate: 2.7 l/h.

The concentrated virus is introduced into the column by gravity; the purification is carried out by means of 20 mM phosphate buffer pH=7.5, 0.1% Tween 80, flow rate: 2.7 l/h.

8) Final Concentration

Under conditions similar to those used during the preceding concentration, the virus peak derived from the gel filtration column is concentrated. The final volume after rinsing is adjusted to 2.5 liters. The concentrated virus is filtered through a 0.2μ Durapore membrane.

This product corresponds to the purified harvest.

9) Inactivation

The inactivation is carried out using formalin at 1/4000 for 14 d at 37° C.

10) Preparation of the Vaccine

The vaccine is produced from the inactivated purified harvest, adsorbed onto aluminium hydroxide, the packaging being carried out according to conventional methods.

We claim:

1. A process for preparing hepatitis A antigens for use in human vaccines consisting essentially of multiplying HAV virus on competent cells, lysing the infected cells, recovering the supernatant, adding a detergent to the supernatant and after a period of time, filtering the supernatant, purifying the supernatant by chromatography on an anion-exchange support means equilibrated in the presence of a detergent under conditions which retain virions and viral capsids, eluting the virions and viral capsids, and subjecting the eluted virions and viral capsids in the presence of detergent to gel filtration and eluting the hepatitis A antigens.

2. The process of claim 1 wherein the detergent is used at a concentration of 0.001 to 5%.

3. The process of claim 1 wherein the detergent is used at a concentration of about 0.1%.

4. The process of claim 1 wherein the lysis is effected by sonication.

5. The process of claim 1 wherein the anion-exchange support chromatography is effected with a buffer containing the detergent and the elution is effected with an eluent containing the detergent.

6. The process of claim 1 wherein the gel filtration is effected on a column equilibrated with a buffer containing the detergent.

7. The process of claim 1 wherein the supernatant is concentrated between the chromatography and the gel filtration.

8. The process of claim 1 wherein the eluent from the gel filtration is concentrated so that the hepatitis A antigens may then be inactivated.

9. A process for preparing hepatitis A antigens for use in human vaccines consisting essentially of multiplying HAV virus on competent cells, lysing the infected cells, recovering the supernatant, adding Tween 80 to the supernatant and, after a period of time, filtering the supernatant, purifying the supernatant by chromatography on anion-exchange support means equilibrated in the presence of Tween 80 under conditions which retain virions and viral capsids, eluting the virions and viral capsids, and subjecting the eluted virions and viral capsids in the presence of Tween 80 to gel filtration and eluting the hepatitis A antigens.

* * * * *

UNITED STATES PATENT AND TRADEMARK OFFICE
CERTIFICATE OF CORRECTION

PATENT NO. : 5,731,187
DATED : March 24, 1998
INVENTOR(S) : Fanget et al

It is certified that error appears in the above-indentified patent and that said Letters Patent is hereby corrected as shown below:

On title page: Item
[73] change "Merteux" to --Merieux--

Signed and Sealed this

Twenty-first Day of July, 1998

Attest:

BRUCE LEHMAN

*Attesting Officer*  *Commissioner of Patents and Trademarks*